United States Patent [19]

Rosenthal et al.

[11] 4,112,949
[45] Sep. 12, 1978

[54] APPARATUS FOR COLLECTING BODY FLUID

[75] Inventors: Arthur Lee Rosenthal, Dover; Marvin Alpern, Glenridge; Charles Edward Meisch, Jersey City, all of N.J.

[73] Assignee: Howmedica Inc., New York, N.Y.

[21] Appl. No.: 741,733

[22] Filed: Nov. 15, 1976

[51] Int. Cl.² .............................................. A61M 1/00
[52] U.S. Cl. ..................................... 128/278; 417/479
[58] Field of Search .............................. 128/276–278, 128/297–306, 281, 350 V, 145.7; 417/479

[56] References Cited

U.S. PATENT DOCUMENTS

| | | | |
|---|---|---|---|
| 2,397,257 | 3/1946 | Goland et al. ........................ | 128/276 |
| 2,432,288 | 12/1947 | Danzinger ............................ | 43/146 |
| 2,965,907 | 12/1960 | Ropecato .............................. | 4/259 |
| 3,032,037 | 5/1962 | Huber .................................... | 128/276 |
| 3,115,138 | 12/1963 | McElvenny et al. ................. | 128/278 |
| 3,376,868 | 4/1968 | Mondiadis ............................ | 128/278 |
| 3,869,086 | 5/1974 | Schachet et al. .................... | 128/278 |

FOREIGN PATENT DOCUMENTS 398,892  3/1966  Switzerland .............................. 128/278

*Primary Examiner*—Robert W. Michell
*Assistant Examiner*—V. Millin
*Attorney, Agent, or Firm*—Pennie & Edmonds

[57] ABSTRACT

Apparatus for collecting body fluid utilizes a condition of negative pressure in a chamber for drawing body fluid from an area of a wound at a relatively constant flow rate. The apparatus includes a piston assembly movable in a housing from a first to a second position under forces of atmospheric pressure acting on the piston assembly. The apparatus further comprises an assembly for enabling operation of the piston assembly including at least one cylinder and piston movable therein by pulling on a hand gripping element attached to the piston to develop a partial vacuum in the cylinder. The piston assembly includes a diaphragm which is movable for maintaining the chamber sealed except through a port adapted for receipt of a tube connecting with said wound. The evacuator apparatus may be re-used by emptying body fluid from the chamber and reenabling the piston assembly.

9 Claims, 4 Drawing Figures

APPARATUS FOR COLLECTING BODY FLUID

BACKGROUND OF THE INVENTION

Postoperative bleeding and the discharge of other fluid, herein referred to collectively as "body fluid," a volume of which may collect in the area of the wound under the theretofore dissected skin flaps, often results in complication of the healing process of the patient and may jeopardize the most carefully executed operative procedure.

For purposes of prevention of the collection of body fluid there have been developed over the years forms of pressure dressing as well as apparatus generally comprising a suction device and a perforated tube received within the tissue of the patient for fluidly connecting the suction device to the wound.

By removal of body fluid from the area of the wound during the first day or two after surgery thereby to maintain the wound in a relatively dry condition swelling may be reduced and medically favorable consequences such as the acceleration of the healing process may be expected.

The present invention is directed to the latter manner and means of postoperative treatment, constituting an improvement over apparatus of the prior art which comprises typically structures both illustrated and disclosed in Swiss Pat. No. 398,892; U.S. Pat. No. 3,115,138 to McElvenny et al.; and U.S. Pat. No. 3,376,868 to Mondiadis, assigned to the assignee of the present invention, now dedicated to the public.

Referring particularly to the Swiss patent, the apparatus includes a collection device having a pair of opposed walls separated by a pleated connecting wall which permits the opposed walls to be moved toward one another. This movement results in an evacuation of the chamber, creating as the opposed walls are moved apart to their original position a negative pressure condition therein. One of the walls sealingly supports a connecting tube which is adapted for connection to a drainage tube, a length of which is formed with a series of perforations through which the body fluid may enter at the situs of the wound. The other of the walls supports a weight whose downward force causes the walls to move apart. The resulting negative pressure of the chamber is communicated to the situs of the wound through the drainage tube and perforations. The Swiss device is stabilized by a hanger. The McElvenny et al. patent is generally similar in overall structure to that of the Swiss device except that it utilizes a series of springs disposed within and acting between opposed walls of the chamber to cause the opposed walls to separate.

The Mondiadis patent is a further representation of the prior art. To this end, Mondiadis discloses a container with a chamber, a connecting tube and a drainage tube for passing body fluid from the area of a wound into the chamber by virtue of the development of a negative pressure therein. In Mondiadis the container which is compressible is formed of a resilient elastomeric material whose memory when the forces are removed causes the walls to return to an uncompressed state as the body fluid is drawn therein through the flow path including the connecting tube.

While each of the apparatus discussed above have received varying degrees of acceptability the apparatus suffer from several disadvantages including ease and manner of operation, difficulty in discharging the fluid from the collecting container, accidentally causing the wound to be inflated, and the inability to maintain a relatively constant flow rate. Thus, the Swiss apparatus, for example, requires a hanger structure, a support for the hanger structure which may prevent ambulation of the patient, as well as a series of weights for developing a negative pressure. While both the apparatus of McElvenny et al. and Mondiadis do not prevent ambulation of the patient, they are adapted for securement on the body, they offer a degree of difficulty in evacuating air from the chamber through compression of the walls while at the same time controlling the port through which the air to be evacuated may pass and attaching a drainage and/or connecting tube to the container. Further, the McElvenny et al. apparatus requires a plurality of springs as described which add bulk to the structure and reduce the available interior space into which the body fluid is drawn. Further, the springs, as the weights in the Swiss apparatus, add unnecessary expense to the apparatus of this type which is disposable after use.

BRIEF DESCRIPTION OF THE INVENTION

The present invention has a primary object to improve over those apparatus discussed above in that it is directed to an evacuator apparatus for drawing body fluid from the tissue within the region of a wound and collecting the withdrawn body fluid in a chamber that is capable of being activated and the fluid that is collected subsequently discharged by the use of only one hand. The evacuator apparatus of the present invention is relatively easy to operate yet it is capable of providing a negative pressure or suction in a drainage tube connecting the wound with the chamber of the evacuator apparatus itself. The evacuator apparatus of the present invention, also, is economical in cost as required by disposable-type devices, is reliable in operation and capable of maintaining negative pressure during a protracted period during which body fluid is withdrawn from the body. As contrasted with devices of the type disclosed by McElvenny et al., the chamber of the present invention is completely available for receipt of body fluid in volumes as may be determined by the size of the evacuator apparatus itself and a relatively consistent flow rate can be obtained during the entire cycle or period of use. Moreover, in the present invention there is no need to provide for discharged air when the apparatus is actuated as in McElvenny. Typically, apparatus of this type are capable of receiving and handling volumes of body fluid of 150 cc's to 400 cc's or more and the flow rate in the prior art tends to significantly decrease as the evacuators are filled.

Typical applications of the evacuator apparatus of the present invention in the surgical field, for example, and not by way of limitation, are:

(1) in large surgical fields developed in operations such as mastectomies and neck dissections, abdominal and perinial and certain chest procedures;

(2) in evacuating hematoma in such operations as upon the hip, femur, tibia, forearm or hand;

(3) to evacuate joint fluid following knee joint operations and the like;

(4) compound fractures;

(5) the treatment of large soft tissue abscesses and the like;

(6) in the treatment of chronic osteomallitis, septic joints, and the like; and (7) other uses as, for example, the replacement of catheters now employed in many situations.

Broadly stated, the evacuator apparatus for use in the surgical fields as set out above thereby to collect body fluid from a closed wound comprises a single-hand activated housing having a fluid receiving chamber whose volumetric capacity increases as the apparatus is actuated by a piston assembly within the housing that is caused to move axially thereof away from an end plate under forces of atmospheric pressure. A diaphragm which substantially is of the outline of the housing seals the chamber from ambient conditions thereby as the piston assembly moves axially of the housing fluids may be drawn into the chamber through an inlet which is normally closed. A support plate secures the diaphragm between it and the underside of a member forming a part of the piston assembly as well as to locate it in a first or unactivated position. A first handle is secured to the housing and it, together with other means as are necessary, sealingly secures the diaphragm to the housing. The piston assembly operates within a cylinder formed by the housing and end plate.

One or more but preferably two power pistons each are movable within a cylinder carried by the upper surface of the member of the piston assembly. The cylinder or cylinders are symmetrically arranged about the axis of the housing and each piston by means of a stem is connected to a second handle or gripping member movable with respect to the first handle when the apparatus is actuated. The handles include intercooperating guide means for alignment of the handles during movement to a position at which the handles interlock by cooperative latching means. When latched the apparatus is fully charged or actuated and a relatively high partial vacuum will have been built up below the piston in each cylinder with the result that the force of atmospheric pressure causes the piston assembly to move upwardly in the housing whereby body fluid may be drawn into the chamber. Since no air is being expelled during actuation, there is no opportunity for the area to be evacuated to become inflated or exposed to air.

There has thus been outlined rather broadly the more important features of the invention in order that the detailed description thereof that follows may be better understood and in order that the present contribution to the art may be better appreciated. There are, of course, additional features of the invention that will be described hereinafter and which will form the subject of the claims appended hereto. Those skilled in the art will appreciate that the conception upon which this disclosure is based may be readily utilized as a basis for the designing of other structures for carrying out the several purposes of the invention. It is important, therefore, that the claims be regarded as including such equivalent constructions as do not depart from the spirit and scope of the invention.

DESCRIPTION OF THE PREFERRED EMBODIMENT

Figure 1:
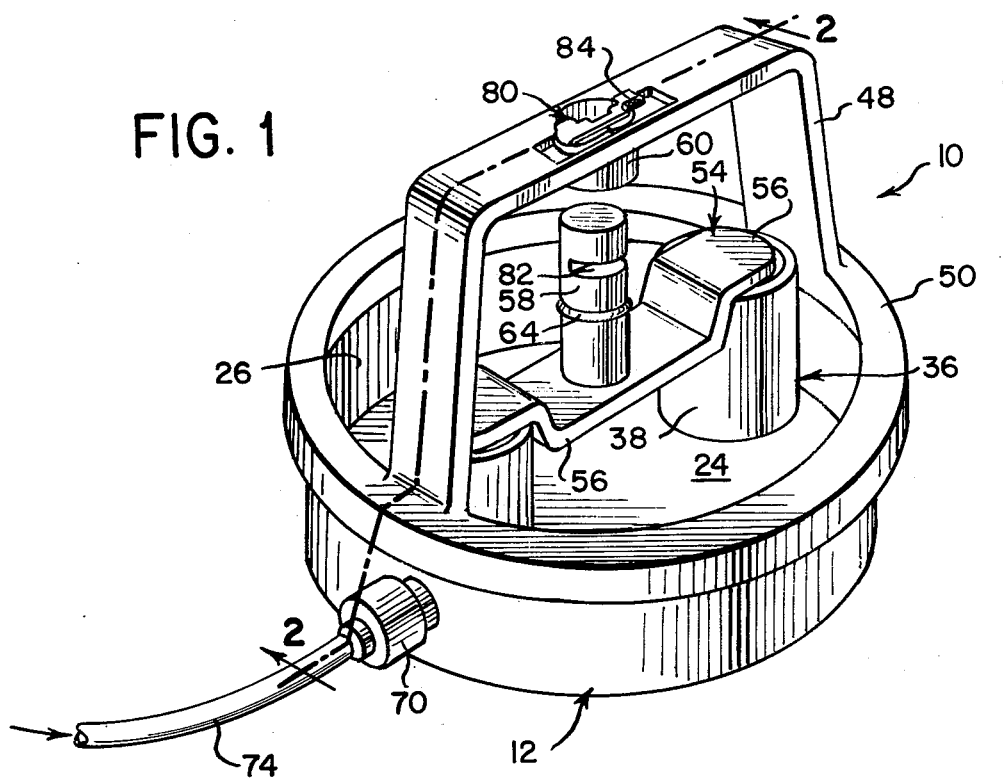
FIG. 1 is a view in perspective of the preferred form of evacuator apparatus of the present invention.
Figure 2:
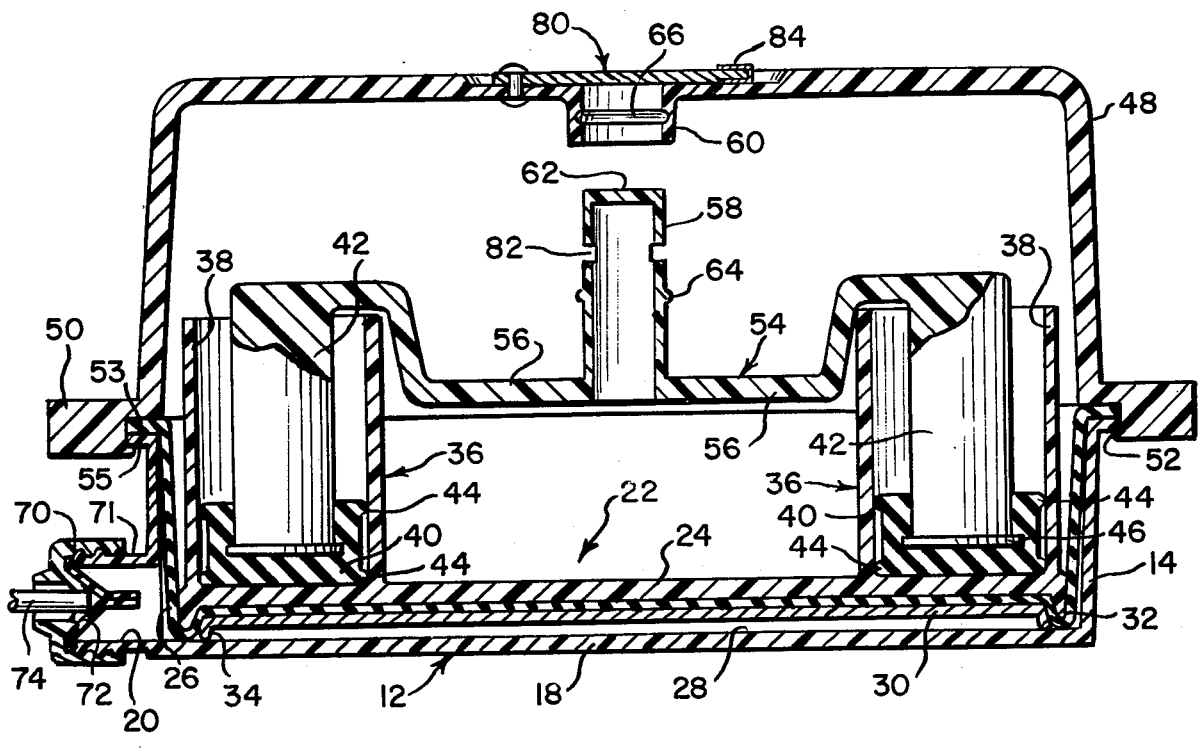
FIG. 2 is a view in vertical section as seen along the line 2—2 in FIG. 1.

The evacuator apparatus generally identified by the numeral 10 may be seen to best advantage in FIGS. 1 and 2. The evacuator apparatus includes a housing 12 formed by a wall 14 terminating in an outwardly directed lip 16 at an open end and closed by an end plate 18. The end plate and wall which extends substantially normal thereto may be integral therewith or otherwise secured by any suitable means around the periphery. A port 20 is formed in the wall within the region of the end plate, the wall otherwise being continuous throughout.

The housing 12 may take any particular form as desired or as may be convenient insofar as manufacturing and operating techniques are concerned. The housing preferably is formed by a substantially rigid wall having a cylindrical outline and closed by a round end plate, as illustrated in FIG. 2.

As will be described in more detail below, the wall and end plate define a cylinder whose internal chamber may be negatively pressurized by action of a piston assembly 22. The piston assembly capable of movement axially relative to the housing includes a member 24 and a diaphragm 26 which is adapted for sealing the chamber 28 around the member from ambient pressure conditions. The member preferably will be of a configuration as that of the end plate although of a somewhat reduced dimension as to be spaced from the inner surface of the wall 14. The diaphragm 26 is accommodated within the spacing such that the piston assembly and particularly the diaphragm have complete freedom of movement. The diaphragm will be formed of a resilient, fluid impermeable material such as rubber or one of the rubber substitutes thereby to permit flexing movement and maintenance of the seal. Diaphragms of this type and for this purpose are well known. The chamber 28 is completely sealed by structure at port 20 to be described.

One, two or more assemblies for enabling operation of the evacuator apparatus are supported by the member 24 of piston assembly 22. These assemblies or enabling assemblies 36 preferably are disposed symmetrically of the member 24. Thus, a single enabling assembly would be located on the longitudinal axis of the evacuator apparatus, while two or more enabling assemblies would be located equiangularly about the longitudinal axis.

The preferred form of evacuator apparatus includes two enabling assemblies 36 each including a cylinder 38 and a piston 40 carried by a stem 42. Each of the cylinders is substantially of like diameter whereby their chambers bounded by the piston, cylinder wall and member 24 serving as an end plate are of equal volumetrical capacity. Each piston may be formed of rubber or one of the common elastomeric materials employed conventionally as a rubber substitute in syringe manufacture. The piston 40 may include a single but preferably a pair of spaced rings 44 engageable with the cylinder wall for stabilizing the positional orientation of the piston during movement in the cylinder and providing a better seal. The piston is mounted on the end of the stem 42 by flexing it over a flange 46.

The evacuator apparatus 10 further includes a handle 48 which may be gripped in a single hand by the user. The handle generally is of domed-shaped outline and terminates in an annular ring 50. The ring provides a cutout 52 in the inner diameter wall bounded by an upper shoulder 53 and lower lip 55 (see FIG. 2). The handle is substantially rigid throughout, yet within the region of the extremes at the annular ring it has a slight degree of resilience such that upon flexing, and release of the annular ring the handle lip 55 is received under the lip 16 of the wall 14 thereby to sealingly and tightly secure diaphragm 26 at its periphery between the shoulder 53 and lip 16.

A gripping member 54 including a pair of arms 56 with lateral offset portions connects both the stems 42 for conjoint controlled movement of pistons 40. The arms extend outwardly from an elongated projection 58. The projection is arranged axially of the evacuator apparatus and cooperates within a guide 60 formed in handle 48. The projection 58 and guide 60 may be of any outline. For example, the projection may be a cylinder or of cylindrical outline with a closed end 62 cylindrical or tapered (not shown), while the guide 60 is complementary thereto. The projection carries a ring 64 between the ends and the guide is formed with an accommodating groove 66. Another form of latching mechanism that can be used either alone or in addition to ring 64 is a latching mechanism depressed in handle 48. As shown in FIG. 1, a spring bias latching mechanism 80 is located in the handle 48 and automatically engages a notch 82 in projection 58. When it becomes necessary to empty the chamber 28, latch protursion 84 is actuated thereby moving the latching mechanism 80 out of engagement with notch 82. Other forms of engaging structures or latching components as are well known may be employed equally as well.

The structures of the evacuator apparatus may be formed of any material but preferably of one of the commonly used plastics as are used in medical-type devices. Thus, the material may be one of the polyolefins such as polypropylene which is somewhat rigid in character, yet has a degree of resilience, may be molded to provide smooth walls thereby to enhance movement, for example, of the piston 40 in cylinder 38, and may be at least translucent thereby to observe the capacity of fill in chamber 28.

Figure 3:
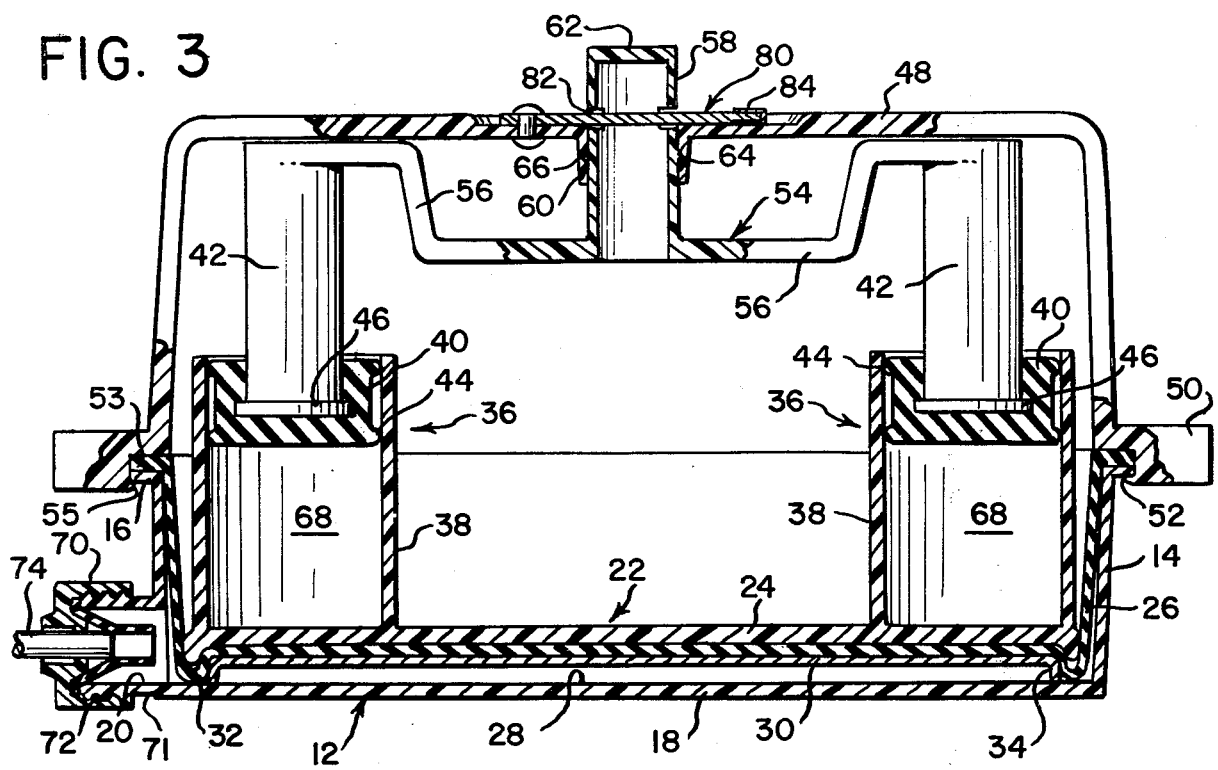
FIGS. 3 and 4 are views similar to the view in FIG. 2 and together with FIG. 2 illustrate sequentially relative positions of the structure of the evacuator apparatus by which a wound may be drained of body fluid.
Figure 4:
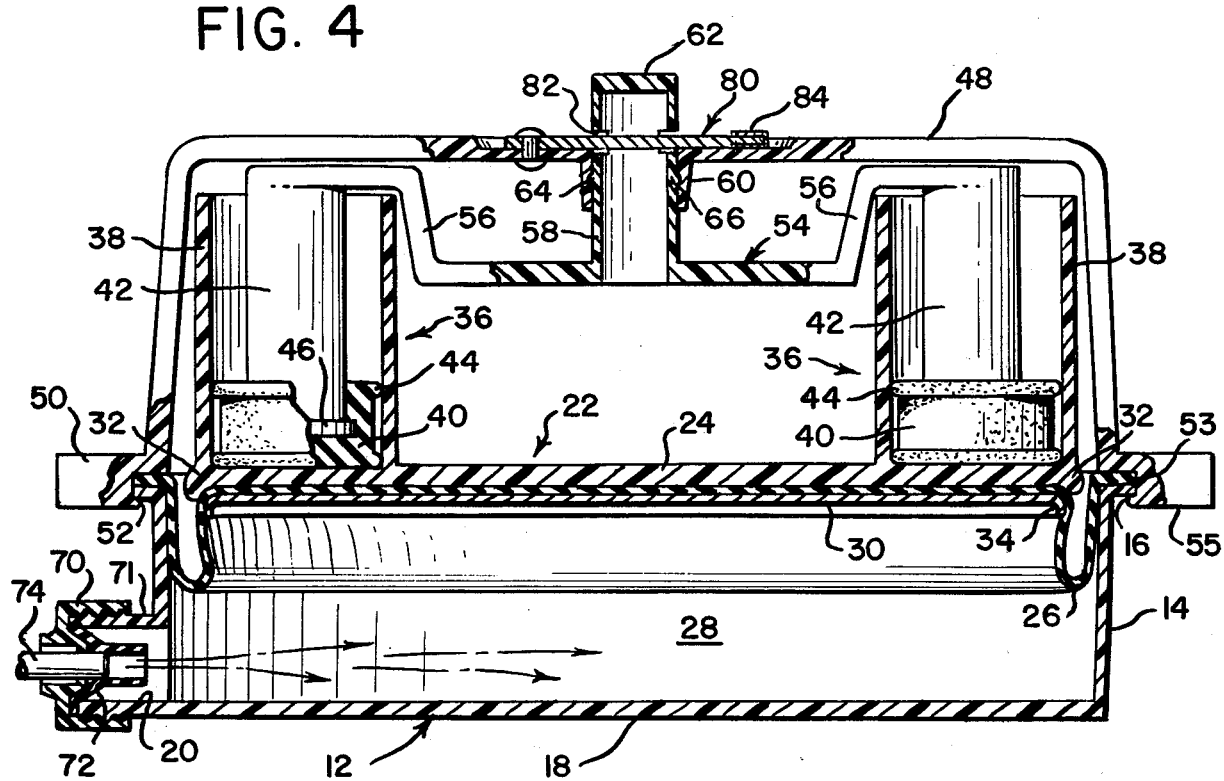

In operation, referring to FIGS. 2–4, the user suitably grasps the gripping member 54 with the fingers, while the thumb and heel of the hand are supported by the handle 48. In this manner the pistons 40 of the enabling assemblies 36 are moved from the position of FIG. 2 to the position of FIG. 3. As may be seen in the latter figure, the pistons, while in sealing engagement, traverse the length of cylinders 38 during this movement for development of a relatively high partial vacuum in the chambers 68, equal to a column of mercury of about 26 mm. in height. In practice, it has been found that the apparatus can be repeatedly fully charged or actuated by using only one hand and irrespective of the operator's strength or variations.

The gripping member 54 is moved through squeezing action relative to the handle 48 until the latching mechanism 80 has engaged notch 82 and/or ring 64 has entered groove 66. Further movement is prevented by the offset portions of arms 56 which have moved into substantially abutting relationship with handle 48.

The port 20 communicating with chamber 28 includes a nozzle 71 of cylindrical outline and externally threaded along a length from the outer end. A closure 70 which may be a "Luer lock" type closure is received on the nozzle for securement of a valve member 72 between a shoulder at the end of the nozzle and the internal walls of the closure. The valve which is schematically illustrated completes the seal of the chamber 28 and is adapted to sealingly receive the end of a tube 74, which is attached (FIG. 4) to the evacuator device. As heretofore set out, the tube connects the chamber 28 with the area of the wound such that body fluid may be drawn from the wound. Thus, the connection of the tube can take place either following actuation or displacement of the enabling assemblies (FIG. 3) or during actuation. Since the present invention does not require the discharge of air within the chamber 28, the wound or area to be evacuated cannot be accidentally inflated.

FIG. 4 illustrates the piston assembly having moved from the first position of FIGS. 2 and 3 to the second position. Movement commences because of the differential pressure acting on the piston assembly such that the force of atmospheric pressure below plate 30 causes the piston assembly to commence movement from the first position. Since tube 74 is connected to the chamber 28 body fluid drawn into the chamber because of suction continues to flow until the chamber is full. It has been found that the present invention provides a relatively constant withdrawal rate of fluid with a minimum of rate decrease through its entire operating cycle. The volumetric capacity may be about 400 cc's or more, as desired.

Movement of the plate 30 and number 24 is followed by the diaphragm 26 which is maintained sealed thereby to permit the creation of negative pressure within the chamber.

Reading of the fluid level can be facilitated by visual inspection of a scale etched directly into the side of wall 14 and does not require discharging or other unusual manipulations to obtain an accurate estimate of the volume of withdrawn fluid.

While the evacuator apparatus 10 is a disposable device, it is contemplated that it may be used a second, third, or more times for purposes of elimination of body fluid from the wound in postoperative care. Thus, the evacuator apparatus may be emptied of body fluid by removal of the closure 70 and valve 72 whereby the contents may be discharged into a receptacle for sanitary disposal. Discharge of body fluid will be by means of port 20. Thereafter, the piston assembly is returned to the FIG. 2 position by pushing down on the gripping member 54 once the ring 64 has disengaged from the latching mechanism. The construction of the piston assembly 22 and exit port 20 permit equalization of atmospheric pressure between piston surface and piston chamber 68, thus allowing for unopposed emptying of fluid from chamber 28 whether an additional downward force is applied to the gripping member 54 for quick fluid expulsion or the apparatus is simply tilted and the fluid discharged in a pouring fashion. A new valve then may be attached within port 20 and the foregoing steps of operation may be carried out anew. Due to the unique configuration and rigidity of the apparatus, the patient is protected against accidental expulsion of previously removed fluid back toward the body.

Having described the invention with particular reference to the preferred form thereof, it will be obvious to those skilled in the art to which the invention pertains after understanding the invention, that various changes and modifications may be made therein without departing from the spirit and scope of the invention as defined by the claims appended hereto.

What is claimed is:

1. Apparatus for collecting body fluid from the area of tissue behind a closed wound, comprising:
   a. a substantially rigid housing having
      (i) side wall means and
      (ii) an end wall connected to said side wall means thereby to close one end of said housing;
   b. piston means axially movable relative to said end wall;
   c. sealing means;
   d. means connecting said sealing means both to said housing and piston means for sealing a chamber bounded substantially by said piston means and housing from ambient pressure conditions;
   e. means supported by said piston means, said supported means being actuatable thereby to create a pressure differential on opposite sides of said piston means for enabling said movement of said piston means relative to said end wall;
   f. means for actuating said supported means whereby said movement of said piston means when said chamber is in substantially closed fluid connection with said area of tissue will create a negative pressure in said chamber to draw said body fluid from said tissue for collection in said chamber;
   g. said supported means including at least one cylindrically walled member, said cylindrically walled member having an axis longitudinal of said axis of movement of said piston means with an end surface formed by a portion of the surface of said piston means, and a piston element adapted for movement away from said end surface for development of a partial vacuum therebelow.

2. The apparatus of claim 1 wherein said supported means includes a pair of cylindrically walled members, said cylindrically walled members being disposed so that their longitudinal axes fall within a plane including said axis of movement of said piston means and at equal radii therefrom.

3. The apparatus of claim 1 further including:
   a. a stationary handle element;
   b. means connecting said handle element and housing; and wherein said actuating means for each walled cylinder includes
   c. a stem;
   d. gripping means connected to said stem and adapted for movement to a second position relatively closer to said stationary handle than a first position; and
   e. means connecting said stem and piston element.

4. The apparatus of claim 3 including latching means for releasably latching said gripping means when said gripping means have moved to said second position, said second position being adjacent said stationary handle.

5. The apparatus of claim 4 wherein said supported means includes a pair of cylindrically walled members disposed symmetrically on said piston means, and said gripping means is formed by a movable handle connected at its ends to said stems.

6. The apparatus of claim 5 wherein said stationary handle spans across said housing substantially in alignment with said movable handle so that the user may grip said movable handle with the fingers while supporting the heel and thumb of the hand by said stationary handle.

7. The apparatus of claim 1 including a stationary handle, and wherein said housing at said open end is formed with an outward lip, said sealing means extending along and juxtaposed to said lip, and said means connecting said sealing means to said housing including a perimetrical cutout in a base of said handle whereby a portion of said base is received under said lip and a portion of said base is received on said sealing means for forcing said sealing means tightly toward said lip.

8. The apparatus of claim 7 wherein said means connecting said sealing means to said piston means includes a plate, means for supporting said plate on said piston means, said sealing means being disposed between said plate and piston means.

9. The apparatus of claim 1 including port means in said housing communicating with said chamber, and means connected to said port means normally closing and sealing said chamber from said ambient pressure conditions yet adapted to receive said body fluid therethrough upon creation of said negative pressure in said chamber.

* * * * *

UNITED STATES PATENT AND TRADEMARK OFFICE
CERTIFICATE OF CORRECTION

PATENT NO. : 4,112,949

DATED : September 12, 1978

INVENTOR(S) : Arthur Lee Rosenthal, Marvin Alpern, and Charles Edward Meisch

It is certified that error appears in the above-identified patent and that said Letters Patent are hereby corrected as shown below:

In the references, "3,869,086" should read --3,809,086--.

In column 5, line 28, "protursion 84" should read --protrusion 84--.

In column 6, line 27, "number 24" should read --member 24--.

Signed and Sealed this

Nineteenth Day of December 1978

[SEAL]

Attest:

RUTH C. MASON
Attesting Officer

DONALD W. BANNER
Commissioner of Patents and Trademarks